United States Patent
Adams et al.

(12) 
(10) Patent No.: US 10,478,602 B2
(45) Date of Patent: Nov. 19, 2019

(54) ANTISEPTIC SWAB WITH ACTIVATION BUTTON

(71) Applicant: iMed Technology, Inc., Dallas, TX (US)

(72) Inventors: Kyle S. Adams, Dallas, TX (US); Gordon E. Atkinson, Black Mountain, NC (US)

(73) Assignee: iMed Technology, Inc., Dallas, TX (US)

( * ) Notice: Subject to any disclaimer, the term of this patent is extended or adjusted under 35 U.S.C. 154(b) by 0 days.

(21) Appl. No.: 15/878,999

(22) Filed: Jan. 24, 2018

(65) Prior Publication Data

US 2019/0224461 A1    Jul. 25, 2019

(51) Int. Cl.
*A61M 35/00* (2006.01)
*A61F 13/40* (2006.01)

(52) U.S. Cl.
CPC ................................. *A61M 35/006* (2013.01)

(58) Field of Classification Search
CPC .................................................. A61M 35/006
USPC ...................................... 401/132–135; 604/3
See application file for complete search history.

(56) References Cited

U.S. PATENT DOCUMENTS

| | | |
|---|---|---|
| 3,414,360 A | 12/1968 | Schwartzman |
| 3,482,920 A | 12/1969 | Schwartzman |
| 3,922,099 A | 11/1975 | Christine et al. |
| 4,148,318 A | 4/1979 | Meyer |
| 4,415,288 A | 11/1983 | Gordon et al. |
| 4,498,796 A | 2/1985 | Gordon et al. |
| 4,730,949 A | 3/1988 | Wilson |
| 4,927,283 A | 5/1990 | Fitjer |
| 5,042,690 A | 8/1991 | O'Meara |
| 5,120,301 A | 6/1992 | Wu |
| 5,769,552 A | 6/1998 | Kelley et al. |
| 6,536,975 B1 | 3/2003 | Tufts |
| 7,121,754 B2 | 10/2006 | Bressler et al. |
| 7,201,525 B2 | 4/2007 | Mohiuddin |
| 8,348,537 B2 | 1/2013 | Cable, Jr. et al. |
| 2002/0076258 A1 | 6/2002 | Crosby et al. |

(Continued)

FOREIGN PATENT DOCUMENTS

EP    0430724 A1    6/1991

OTHER PUBLICATIONS

U.S. Appl. No. 15/285,760 entitled "Antiseptic Swab", filed Oct. 5, 2016 by Kyle S. Adams et al.

(Continued)

*Primary Examiner* — David J Walczak
*Assistant Examiner* — Joshua R Wiljanen
(74) *Attorney, Agent, or Firm* — Stevens & Showalter, LLP

(57) ABSTRACT

A liquid dispensing device includes a handle having a hollow interior defining a fluid reservoir. A base member is affixed to the lower end of the handle and has a bottom surface, and a frangible cover is secured over the bottom surface and forms a seal across the opening of the fluid reservoir. A swab head comprising an absorbent sponge-like member and a button element is supported on the base member. The sponge-like member has opposing outer and inner sides wherein the inner side is affixed to the base member. The button element includes a foot portion at a first longitudinal end adjacent to the outer side of the sponge-like member and includes a penetration end at an opposing second longitudinal end of the button element.

20 Claims, 4 Drawing Sheets

(56) References Cited

U.S. PATENT DOCUMENTS

| | | |
|---|---|---|
| 2004/0067090 A1 | 4/2004 | Budds et al. |
| 2004/0162533 A1 | 8/2004 | Alley |
| 2004/0179888 A1 | 9/2004 | Tufts et al. |
| 2006/0039742 A1 | 2/2006 | Cable, Jr. et al. |
| 2007/0231051 A1 | 10/2007 | Flores et al. |
| 2007/0248399 A1 | 10/2007 | Tufts et al. |
| 2008/0058863 A1 | 3/2008 | Quintero et al. |
| 2010/0168638 A1 | 7/2010 | Korogi et al. |
| 2012/0219347 A1 | 8/2012 | Law et al. |
| 2013/0156486 A1 | 6/2013 | Guzman et al. |
| 2015/0050065 A1 | 2/2015 | Guzman |
| 2015/0297876 A1 | 10/2015 | Lockwood et al. |
| 2016/0106964 A1 | 4/2016 | Quaglia |
| 2017/0164713 A1 | 6/2017 | Davia |
| 2017/0165463 A1 | 6/2017 | Law |

OTHER PUBLICATIONS

Design U.S. Appl. No. 29/634,725 entitled "Antiseptic Swab", filed Jan. 24, 2018, by Kyle S. Adams et al.

Oliver, Bradley S.; Notice of Allowance; U.S. Appl. No. 15/285,760, dated Feb. 21, 2018; United States Patent and Trademark Office; Alexandria, VA.

Rapp, Alexander; International Search Report and Written Opinion of the International Searching Authority; International Application No. PCT/US2019/014957; dated Jul. 17, 2019; European Patent Office; Rijswijk, Netherlands.

ANTISEPTIC SWAB WITH ACTIVATION BUTTON

FIELD OF THE INVENTION

The present application relates generally to liquid dispensers and applicators of the type wherein a premeasured supply of liquid is disposed in an applicator handle for selective dispensing. The device described herein has particular applicability to dispensing of antiseptic solution.

BACKGROUND OF THE INVENTION

Tools for surgical preparations generally may include a sponge which is used by medical personnel to apply an antiseptic solution to a patient's skin. The sponge can be dipped into an antiseptic solution in a container and swabbed onto the patient's skin to prevent live bacteria from entering an incision or wound of the skin. Other devices have been developed that contain an antiseptic solution contained in the device for dispensing the solution from an applicator associated with the device. There is a continuing need for a dispensing device that can be configured for use to dispense a fluid, such as an antiseptic solution, to an applicator swab wherein required manipulation of the device prior to use may be minimized.

SUMMARY OF THE INVENTION

In accordance with one aspect of the invention, a liquid dispensing device is provided comprising an elongated member defining a handle having a hollow interior, the hollow interior defining a fluid reservoir having an opening at a lower end of the elongated member. A base member is affixed to the lower end of the elongated member and has a bottom surface, and a frangible cover is secured over the bottom surface and forms a seal across the opening of the fluid reservoir. A swab head is provided comprising an absorbent sponge-like member and a button element, the sponge-like member having opposing outer and inner sides wherein the inner side is affixed to the base member. The button element defines a longitudinal axis and includes a foot portion at a first longitudinal end of the button element adjacent to the outer side of the sponge-like member and a penetration end at an opposing second longitudinal end of the button element.

The penetration end of the button element may comprise a tapered end defining an angle with an apex at a point located at the second longitudinal end of the button element.

The button element may include a peripheral wall extending longitudinally from the first longitudinal end toward the second longitudinal end, and a plurality of longitudinally elongated grooves may extend in from the peripheral wall toward the longitudinal axis.

The button element may be generally circular about the longitudinal axis and the plurality of grooves may be circumferentially spaced around the peripheral wall.

A cavity may be formed in the sponge-like member and the button element may be located within the cavity.

The penetration end of the bottom element may be conical.

Wells may be provided extending from the second longitudinal end toward the first longitudinal end for receiving liquid and for transferring liquid from the wells to the sponge-like member.

Each well may include an open end adjacent to the penetration end and may include a well floor adjacent to the first longitudinal end of the button element, the well floor restricting fluid from flowing through the first longitudinal end.

The sponge-like member may have a compressed state and an uncompressed state, and the second longitudinal end of the button element may be located between the inner and outer sides of the sponge-like member when the sponge-like member is in the uncompressed state.

The second longitudinal end of the button element may be located extending through the frangible cover when the sponge-like member is in the compressed state.

The first longitudinal end of the button element may be exposed adjacent to the outer side of the sponge-like member.

In accordance with another aspect of the invention, a liquid dispensing device is provided comprising an elongated member defining a handle having a hollow interior, the hollow interior defining a fluid reservoir having an opening at a lower end of the elongated member. A base member is affixed to the lower end of the elongated member and has a bottom surface, and a frangible cover is secured over the bottom surface and forms a seal across the opening of the fluid reservoir. A swab head is provided comprising an absorbent sponge-like member and a button element, the sponge-like member having opposing outer and inner sides wherein the inner side is affixed to the base member. A cavity is formed in the sponge-like member extending between the outer and inner sides. The button element is located within the cavity and defines a longitudinal axis. The button element includes a foot portion at a first longitudinal end of the button element adjacent to the outer side of the sponge-like member and a penetration end at an opposing second longitudinal end of the button element. A plurality of elongated fluid receiving grooves comprising wells extend longitudinally into the button element from the second longitudinal end toward the first longitudinal end.

The penetration end of the button element may comprise a tapered end defining an angle with an apex at a point located at the second longitudinal end of the button element, and the wells may extend through at least a portion of the tapered end.

The foot portion may comprise a cylindrical peripheral wall extending from the first longitudinal end toward the second longitudinal end.

The plurality of wells may be circumferentially spaced around the peripheral wall.

The plurality of longitudinally elongated grooves may extend in from the peripheral wall toward the longitudinal axis.

Each well may include an open end adjacent to the penetration end and a well floor adjacent to the first longitudinal end of the button element, the well floor restricting fluid from flowing through the first longitudinal end.

In accordance with a further aspect of the invention, a liquid dispensing device is provided comprising an elongated member defining a handle having a hollow interior, the hollow interior defining a fluid reservoir having an opening at a lower end of the elongated member. A base member is affixed to the lower end of the elongated member and has a bottom surface, and a frangible cover is secured over the bottom surface and forms a seal across the opening of the fluid reservoir. A solution is contained within the fluid reservoir. A swab head is provided comprising an absorbent sponge-like member and a button element, the sponge-like member having opposing outer and inner sides wherein the inner side is affixed to the base member. A cavity is formed in the sponge-like member and extends between the outer and inner sides. The button element is located within the cavity and defines a longitudinal axis. The button element includes a foot portion at a first longitudinal end of the button element adjacent to the outer side of the sponge-like member and a penetration end at an opposing second longitudinal end of the button element. A plurality of elongated fluid receiving grooves comprising wells extend longitudinally into the button element from the second longitudinal end toward the first longitudinal end.

The sponge-like member may have a compressed state and an uncompressed state, and the second longitudinal end of the button element may be located between the inner and outer sides of the sponge-like member when the sponge-like member is in the uncompressed state.

A substantially rigid cover may be provided positioned over the sponge-like member preventing movement from the uncompressed state, the cover may include an outer wall extending along an outer peripheral surface of the sponge-like member between the outer and inner sides and located for engagement with the base member.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
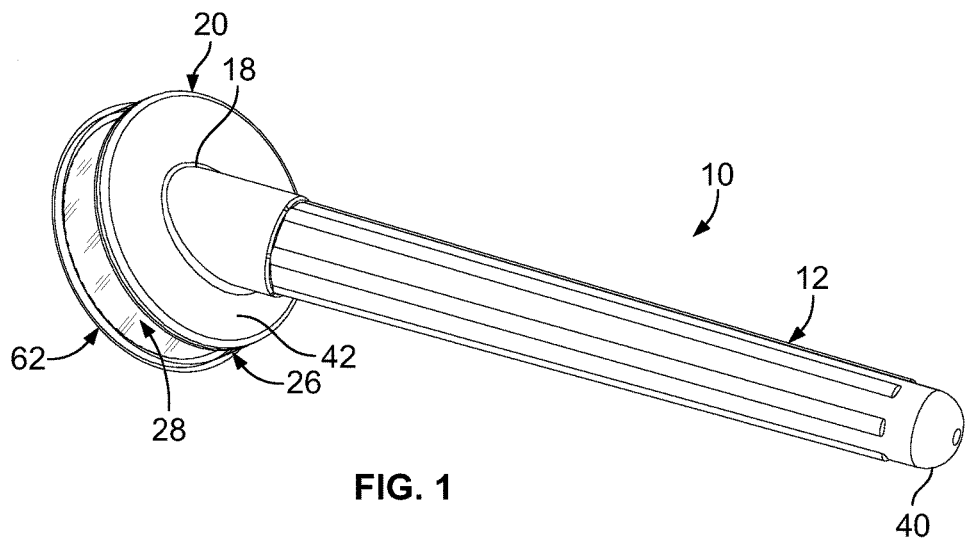
FIG. 1 is a perspective view of a liquid dispensing device in accordance with aspects of the present invention.

Aspects of the invention are illustrated in a first configuration as shown in FIGS. 1-6. Referring initially to FIG. 1, a liquid dispensing device 10 is shown and, in a particular useful configuration, is provided as an antiseptic swab such as may be implemented in medical applications, e.g., as a surgical scrub. The device 10 includes an elongated member defining a handle 12 having a hollow interior. As may be further seen in FIG. 3, the hollow interior defines a fluid reservoir 14 having an opening 16 at a lower end 18 of the handle 12.

Figure 2:
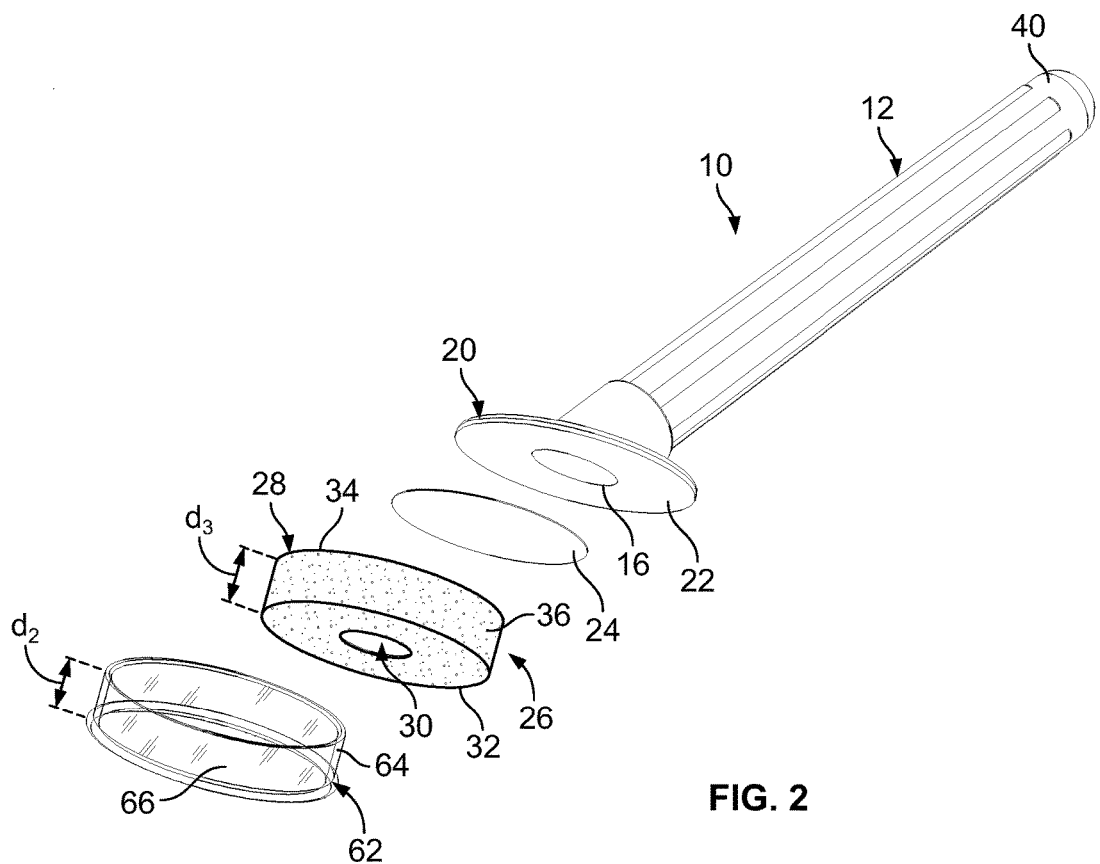
FIG. 2 is an exploded perspective view of the liquid dispensing device shown in FIG. 1.
Figure 3:
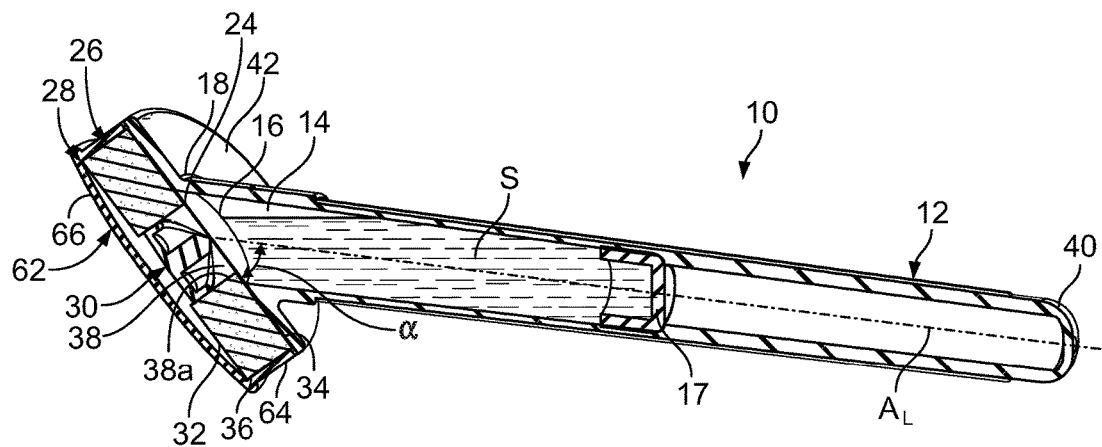
FIG. 3 is a perspective cross-sectional view of the liquid dispensing device shown in FIG. 1.

Referring to FIGS. 2 and 3, a base member 20 is affixed to the lower end 18 of the handle 12 and has a bottom surface 22 facing in a direction away from the handle 12. A cover member comprising a frangible cover 24 is adhered or otherwise secured over at least a portion of the bottom surface 22 and forms a fluid tight seal across and surrounding the opening 16 of the fluid reservoir 14. The frangible cover 24 is a part of the base member 20 that is capable of being broken. A swab head 26 is supported to the base member 20 and comprises an absorbent sponge-like member 28 and a button element 30. The sponge-like member 28 is illustrated as having a cylindrical configuration including a generally planar outer side 32, an opposing generally planar inner side 34, and an outer peripheral surface 36 extending between the outer and inner sides 32, 34, wherein the inner side 34 is affixed to the bottom surface 22 of the base member 20, such as by use of an adhesive.

A cavity 38 (FIG. 3) is defined in the center of the sponge-like member 28, and can be defined by a thru-hole extending between the outer and inner sides 32, 34. The cavity 38 can have a shape that corresponds to the shape of the opening 16, e.g., a circular shape, and the cavity 38 is aligned with the opening 16. The button element 30 is positioned in the cavity 38 and provides a membrane puncturing function and a flow control function, as is described further below.

In the illustrated embodiments, the handle 12 has a cylindrical configuration which is hollow at least in the region of the fluid reservoir 14 adjacent to the base member 20, and can be hollow along the length of the handle 12 between the base member 20 and an outer end 40 of the handle 12 to form the fluid reservoir 14 for permitting the handle to be filled with a fluid, such as an antiseptic solution. The hollow interior of the handle 12 can be partitioned by a plug element 17 (FIG. 3) that may be a hollow cylindrical element having a closed end positioned in an interference fit within the handle 12. The plug element 17 can be positioned to define a predetermined reservoir volume between the base member 20 and the plug element 17 for containing a solution S within the handle 12.

The base member 20 can be attached or integrally formed on the lower end 18 of the handle 12, and the base member 20 is oriented at an angle relative to the handle 12. In a preferred construction of the device 10, the device 10 may be formed of a molded construction and may be molded of, for example, polypropylene or ABS. In the illustrated configuration, as seen in FIG. 3, the base member 20 is oriented with the plane of its bottom surface 22 oriented at a 50 degree angle $\alpha$ relative to a longitudinal axis $A_L$ of the handle 12. It may be noted that the base member 20 may be formed as a plate-like planar member defined by the planar bottom surface 22 and having an opposing upper surface 42 extending laterally from the handle 12. Also, the base member 12 may have a circular configuration centered on the axis $A_L$ of the handle 12, as illustrated herein, or may comprise some other shape. However, the circular shape is preferred for providing a uniform distribution of fluid throughout the sponge-like member 28.

Figure 4:
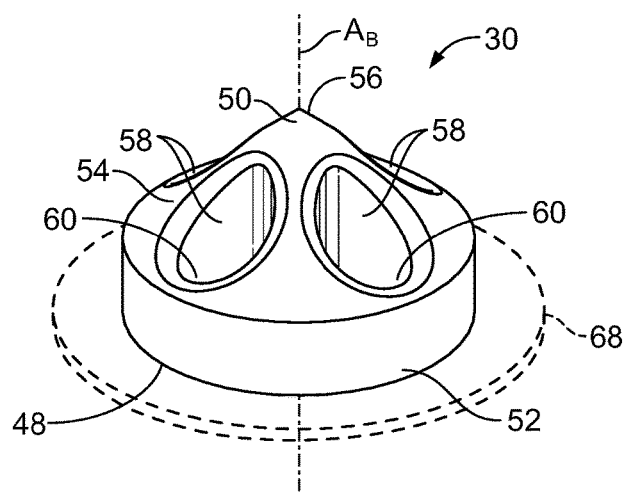
FIG. 4 is a perspective view of a button element for the liquid dispensing device.
Figure 5:
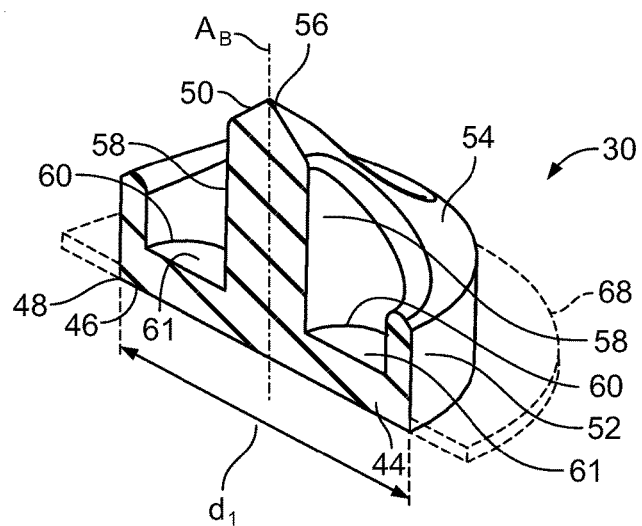
FIG. 5 is a perspective cross-sectional view of the button element shown in FIG. 4.

The button element 30 is preferably a rigid or non-compressible member, and may be formed of a molded construction of, for example, polypropylene or ABS. Referring to FIGS. 4 and 5, the button element 30 is illustrated as having a circular cross-section formed about a longitudinal axis AB and having a diameter $d_1$ that is the same as or slightly greater than the diameter of the thru-hole forming the cavity 38. The button element 30 includes a circular foot portion 44 defining a planar outer surface 46 at a first longitudinal end 48 of the button element 30. A second longitudinal end 50 of the button element 30 defines a penetration end for rupturing the frangible cover 24. The planar outer surface 46 is positioned adjacent to the outer side 32 of the sponge-like member 28, and may be co-planar, or substantially co-planar, with the outer side 32, as seen in FIGS. 2 and 3. The second longitudinal end 50 of the button element 30 is located between the outer and inner sides 32, 34 of the sponge-like member 28 and is preferably positioned adjacent to, but spaced inwardly from, the inner side 34 of the sponge-like member 28.

The foot portion 44 comprises a cylindrical peripheral wall 52 extending from the first longitudinal end 48 toward the second longitudinal end 50. The penetration end comprises a tapered end 54, e.g., a conical surface, extending from the peripheral wall 52 and defining an angle with an apex 56 at a point located at the second longitudinal end 50 of the button element 30.

A plurality of elongated fluid receiving grooves 58 extend longitudinally into the button element 30 from the second longitudinal end 50 toward the first longitudinal end 48. In the illustrated embodiment, four grooves 58 are formed in the button element 30 and are uniformly spaced around the circumference of the button element 30. The grooves 58 define wells 60 extending through at least a portion of the tapered end 54 and into the foot portion 44 for receiving solution S from the fluid reservoir 14. Each well 60 includes an open end adjacent to the penetration end, i.e., the second longitudinal end 50, and a well floor 61 adjacent to the first longitudinal end 48 of the button element 30, the well floor 61 restricting fluid from flowing through the first longitudinal end 48.

The grooves 58 shown in FIGS. 3 and 4 are depicted as circular grooves, and are fully enclosed within the circumference of the peripheral wall 52. The grooves 58 function as fluid conduits or passages for conveying the solution S down into the sponge-like member 28, enabling a substantially uniform distribution of the solution S through the sponge-like member 28 for application of the solution S from the outer side 32, i.e., an application side of the sponge-like member 28, to a treatment area on a patient. The sponge-like member 28 can be formed of an open-cell foam that can permit controlled flow of fluid to the outer side 32 of the sponge-like member 28. It should be understood that other materials may be provided for the sponge-like member 28 including sponges and fibrous materials.

The frangible cover 24 forms a seal over the opening 16 of the fluid reservoir 14 to seal in the antiseptic solution S (FIG. 3). The frangible cover 24 is a thin membrane material and may be formed, for example, of aluminum foil or a plastic sheet. The device 10 may be supplied to a user, e.g., to medical personnel, with antiseptic solution S prepackaged in the fluid reservoir 14 and with a substantially rigid outer cover 62 positioned over the sponge-like member 28 preventing movement from an uncompressed state, as illustrated in FIGS. 1 and 3. The outer cover 62 may be formed of a plastic material, such as ABS. The outer cover 62 includes an outer wall 64 extending along the outer peripheral surface 36 of the sponge-like member 30 between the outer and inner sides 32, 34.

The outer cover 62 also includes an end wall 66 formed integrally with one end of the outer wall 64. The outer wall 64 is formed with a height dimension $d_2$ (FIG. 2) that is approximately equal to a height dimension $d_3$ between the outer and inner sides 32, 34 of the sponge-like member 28. The outer wall 64 can be formed with a dimension, e.g., a diameter, that is at least slightly less than a dimension, e.g., an outer diameter, of the base member 20 for engaging against the base member 20 to form a stop preventing the end wall 66 from compressing the sponge-like member 28. Further, an inner diameter of the outer wall 64 can be slightly less than an outer diameter of the outer peripheral surface of the sponge-like member 28 to frictionally retain the outer cover 62 in position on the swab head 26.

Figure 6:
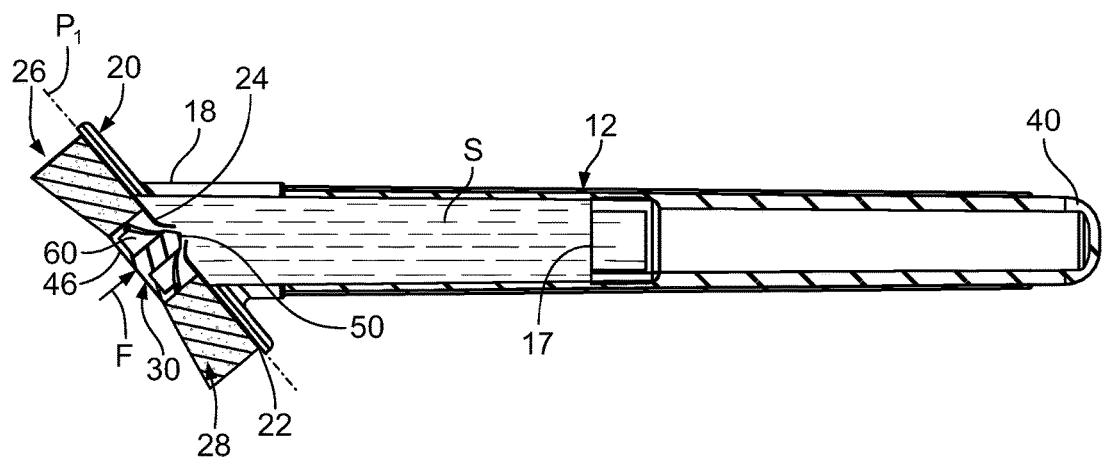
FIG. 6 is an elevational cross-sectional view of the liquid dispensing device illustrating the button element displaced to rupture a cover membrane for a dispensing operation.

In preparation for use, the device 10 may be oriented by holding the handle 12 with the base member 20 located upward, and the outer cover 62 is removed from the swab head 26. A user can then press on the planar outer surface 46 of the button element 30, applying a force in the direction F, as illustrated in FIG. 6. The force F applied to the button element 30 causes at least a portion of the sponge-like member 28, e.g., a center portion, to move from an uncompressed state to a compressed state, depicted in FIG. 6, as the button element 30 moves toward the base member 20. Further, as the button element 30 moves toward the base member 20, the second end 50 of the button element 30 is positioned beyond a plane $P_1$ defined by the frangible cover 24 and the bottom surface 22 of the base member 20. During movement of the button element 30, the penetration end, i.e., the second longitudinal end 50, of the button element 30 engages and ruptures or pierces the frangible cover 24, placing the inner side 34 of the sponge-like member 30 in fluid communication with the fluid reservoir 14. The fluid passages formed by the grooves 58 are also placed in fluid communication with the fluid reservoir 14. Hence, the button element 30 operates as an activation button that provides a rigid surface for a user to engage to start the flow of fluid within the device 10. The compressed state of the sponge-like member 28 corresponds to a position of the button element 30 where the second longitudinal end 50 extends beyond the plane $P_1$ at least a sufficient distance for the penetration end of the button element 30 to rupture the frangible cover 24.

Hence, the button element 30 operates as an activation button that provides a rigid surface for a user to engage to start the flow of fluid within the device 10. The planar outer surface 46 preferably has a substantial surface area similar to or greater than the surface area of a user's fingertip. Also, it should be noted that the swab head 26 may alternatively be configured with the planar outer surface 46 of the button element 30 embedded in the sponge-like member 28, but located close to the outer side 32, such that a thin layer of the sponge-like member 28 could cover the planar outer surface 46.

Further, the button element 30 may be formed with a skirt portion 68 extending radially outward from the peripheral wall 52, near the planar outer surface 46, as depicted by dotted lines in FIGS. 4 and 5. When the button element 30 having the skirt portion 68 is in position on the sponge-like member 28, the skirt portion 68 extends radially outward from the wall 38a defining the cavity 38. The skirt portion 68 can form a broader base for engagement by a user's fingertip. Additionally, engagement of the skirt portion 68 with the outer side 32 of the sponge-like member 28 can facilitate maintaining the button element 30 in position longitudinally relative to the cavity 38 as the button element 30 is actuated to rupture the frangible cover 24.

Orienting the handle 12 with the base member 20 located downward allows the solution S to flow out of the fluid reservoir 14 and into the sponge-like member 28. Additionally, solution S flowing into the grooves 58 and associated wells 60 and flowing through the wall or surface 38a defining the cavity 38 facilitates flow of the solution S into the sponge-like member 28 by providing a reservoir of solution S in the button element 30 that can flow from the grooves 58 and enter the sponge-like member 28 through the cylindrical wall 38a of the cavity 38.

Figure 7:
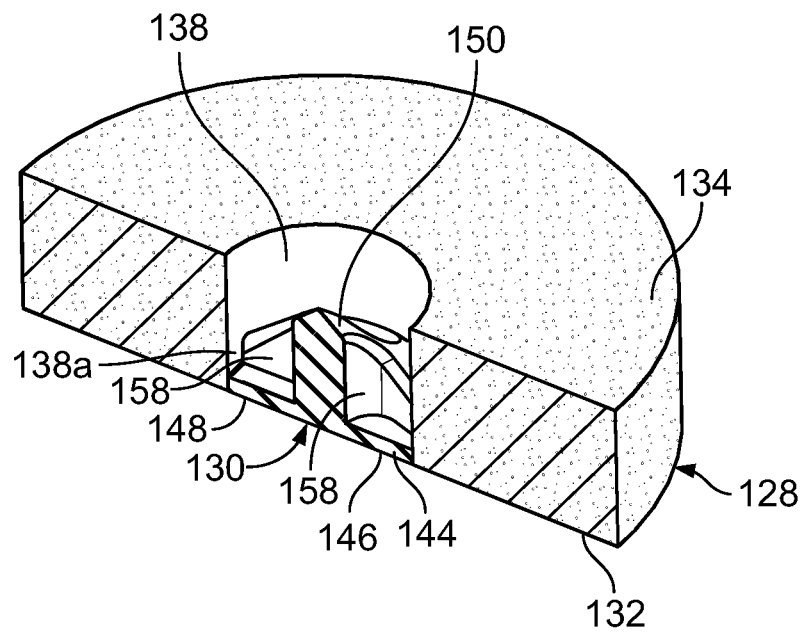
FIG. 7 is a perspective cross-sectional view of an alternative configuration for a button element in association with a sponge-like member of the liquid dispensing device.
Figure 8:
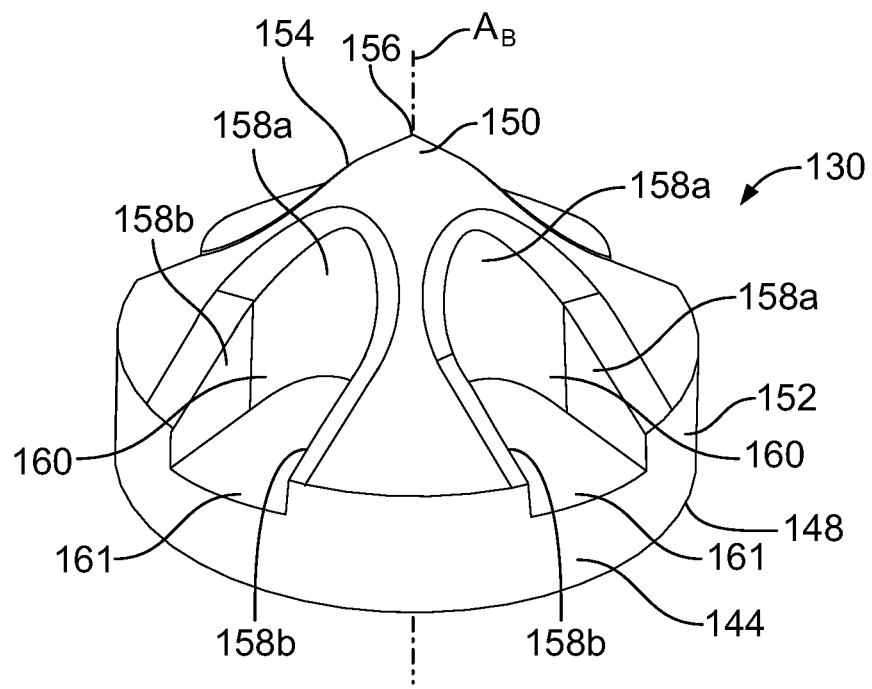
FIG. 8 is a perspective view of the button element of FIG. 7.

Referring to FIGS. 7 and 8, an alternative configuration of a button element is shown. Elements of the alternative configuration corresponding to elements described with reference to FIGS. 1-6 are labeled with the same reference numerals increased by 100, and in FIG. 7 the alternative configuration button element 130 is shown in relation to a sponge-like member 128 having a construction that is substantially similar to that described above for the sponge-like member 28.

The button element 130 includes a circular foot portion 144 defining a planar outer surface 146 at a first longitudinal end 148 of the button element 130. A second longitudinal end 150 of the button element 130 defines a penetration end for rupturing the frangible cover 24 (FIG. 2). The planar outer surface 146 is positioned adjacent to an outer side 132 of the sponge-like member 128, and may be co-planar, or substantially co-planar, with the outer side 132. The second longitudinal end 150 of the button element 130 is located between the outer and inner sides 132, 134 of the sponge-like member 128 and is preferably positioned adjacent to, but spaced inwardly from, the inner side 134 of the sponge-like member 128.

The foot portion 144 comprises a cylindrical peripheral wall 152 extending from the first longitudinal end 148 toward the second longitudinal end 150. The penetration end comprises a tapered end 154, e.g., a conical surface, extending from the peripheral wall 152 and defining an angle with an apex 156 at a point located at the second longitudinal end 150 of the button element 130.

A plurality of elongated fluid receiving grooves 158 extend longitudinally into the button element 130 from the second longitudinal end 150 toward the first longitudinal end 148. Further, the elongated grooves 158 extend radially in from the peripheral wall 152 toward a longitudinal axis AB of the button element 130. In particular, the grooves 158 can include a curved inner portion 158a, such as a semi-circular portion, and a pair of generally straight outer portions 158b wherein the outer portions 158b extend from the inner portion 158a to the peripheral wall 152. The grooves 158 define wells 160 extending through at least a portion of the tapered end 154 and into the foot portion 144 for receiving solution S from the fluid reservoir 14 (FIG. 3). Each well 160 includes an open end adjacent to the penetration end, i.e., the second longitudinal end 150, and a well floor 161 adjacent to the first longitudinal end 148 of the button element 130. The well floor 161 restricts fluid from flowing through the first longitudinal end 148. Further, when the button element 130 is assembled into the sponge-like member 128, a wall or surface 138a of the sponge-like member 128 defining the cavity 138 forms a radially outer boundary for the well 160 along at least the foot portion 144 of the button element 130.

The grooves 158 function as fluid conduits or passages for conveying the solution S down into the sponge-like member 128, enabling a substantially uniform distribution of the solution S through the sponge-like member 128 for application of the solution S from the outer side 132, i.e., an application side, to a treatment area on a patient.

The configuration of FIGS. 7 and 8 operates in a manner similar to that described for the configuration of FIGS. 1-6. As a user presses on the planar outer surface 146 of the button element 130, the penetration end of the button element 130 moves into engagement with the frangible cover 24 to rupture the frangible cover 24, placing the inner side 134 of the sponge-like member 130 in fluid communication with the fluid reservoir 14. The fluid passages formed by the grooves 158 are also placed in fluid communication with the fluid reservoir 14 for distribution of the solution S to the surface 138a defining the cavity 138 in the sponge-like member 128.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid dispensing device comprising:
an elongated member defining a handle having a hollow interior, the hollow interior defining a fluid reservoir having an opening at a lower end of the elongated member;
a base member affixed to the lower end of the elongated member and having a bottom surface;
a frangible cover secured over the bottom surface and forming a seal across the opening of the fluid reservoir;
a swab head comprising an absorbent sponge-like member and a button element, the sponge-like member having opposing outer and inner sides wherein the inner side is affixed to the base member; and
the button element defining a longitudinal axis, the button element including a foot portion at a first longitudinal end of the button element adjacent to the outer side of the sponge-like member and a penetration end at an opposing second longitudinal end of the button element.

2. The liquid dispensing device as set forth in claim 1, wherein the penetration end of the button element comprises a tapered end defining an angle with an apex at a point located at the second longitudinal end of the button element.

3. The liquid dispensing device as set forth in claim 2, wherein the penetration end of the bottom element is conical.

4. The liquid dispensing device as set forth in claim 1, wherein the button element includes a peripheral wall extending longitudinally from the first longitudinal end toward the second longitudinal end, and a plurality of longitudinally elongated grooves extend in from the peripheral wall toward the longitudinal axis.

5. The liquid dispensing device as set forth in claim 4, wherein the button element is generally circular about the longitudinal axis and the plurality of grooves are circumferentially spaced around the peripheral wall.

6. The liquid dispensing device as set forth in claim 1, wherein a cavity is formed in the sponge-like member and the button element is located within the cavity.

7. The liquid dispensing device as set forth in claim 1, including wells extending from the second longitudinal end toward the first longitudinal end for receiving liquid and for transferring liquid from the wells to the sponge-like member.

8. The liquid dispensing device as set forth in claim 7, wherein each well includes an open end adjacent to the penetration end and a well floor adjacent to the first longitudinal end of the button element, the well floor restricting fluid from flowing through the first longitudinal end.

9. The liquid dispensing device as set forth in claim 1, wherein the sponge-like member has a compressed state and an uncompressed state, and the second longitudinal end of the button element is located between the inner and outer sides of the sponge-like member when the sponge-like member is in the uncompressed state.

10. The liquid dispensing device as set forth in claim 9, wherein the second longitudinal end of the button element is located extending through the frangible cover when the sponge-like member is in the compressed state.

11. The liquid dispensing device as set forth in claim 1, wherein the first longitudinal end of the button element is exposed adjacent to the outer side of the sponge-like member.

12. A liquid dispensing device comprising:
   an elongated member defining a handle having a hollow interior, the hollow interior defining a fluid reservoir having an opening at a lower end of the elongated member;
   a base member affixed to the lower end of the elongated member and having a bottom surface;
   a frangible cover secured over the bottom surface and forming a seal across the opening of the fluid reservoir;
   a swab head comprising an absorbent sponge-like member and a button element, the sponge-like member having opposing outer and inner sides wherein the inner side is affixed to the base member;
   a cavity formed in the sponge-like member extending between the outer and inner sides;
   the button element located within the cavity and defining a longitudinal axis, the button element including a foot portion at a first longitudinal end of the button element adjacent to the outer side of the sponge-like member and a penetration end at an opposing second longitudinal end of the button element; and
   a plurality of elongated fluid receiving grooves comprising wells extending longitudinally into the button element from the second longitudinal end toward the first longitudinal end.

13. The liquid dispensing device as set forth in claim 12, wherein the penetration end of the button element comprises a tapered end defining an angle with an apex at a point located at the second longitudinal end of the button element, and the wells extend through at least a portion of the tapered end.

14. The liquid dispensing device as set forth in claim 13, wherein the foot portion comprises a cylindrical peripheral wall extending from the first longitudinal end toward the second longitudinal end.

15. The liquid dispensing device as set forth in claim 14, wherein the plurality of wells are circumferentially spaced around the peripheral wall.

16. The liquid dispensing device as set forth in claim 14, wherein the plurality of longitudinally elongated grooves extend in from the peripheral wall toward the longitudinal axis.

17. The liquid dispensing device as set forth in claim 12, wherein each well includes an open end adjacent to the penetration end and a well floor adjacent to the first longitudinal end of the button element, the well floor restricting fluid from flowing through the first longitudinal end.

18. A liquid dispensing device comprising:
   an elongated member defining a handle having a hollow interior, the hollow interior defining a fluid reservoir having an opening at a lower end of the elongated member;
   a base member affixed to the lower end of the elongated member and having a bottom surface;
   a frangible cover secured over the bottom surface and forming a seal across the opening of the fluid reservoir;
   a solution contained within the fluid reservoir;
   a swab head comprising an absorbent sponge-like member and a button element, the sponge-like member having opposing outer and inner sides wherein the inner side is affixed to the base member;
   a cavity formed in the sponge-like member extending between the outer and inner sides;
   the button element located within the cavity and defining a longitudinal axis, the button element including a foot portion at a first longitudinal end of the button element adjacent to the outer side of the sponge-like member and a penetration end at an opposing second longitudinal end of the button element; and
   a plurality of elongated fluid receiving grooves comprising wells extending longitudinally into the button element from the second longitudinal end toward the first longitudinal end.

19. The liquid dispensing device as set forth in claim 18, wherein the sponge-like member has a compressed state and an uncompressed state, and the first longitudinal end of the button element is located between the inner and outer sides of the sponge-like member when the sponge-like member is in the uncompressed state.

20. The liquid dispensing device as set forth in claim 19, including a substantially rigid cover positioned over the sponge-like member preventing movement from the uncompressed state, the cover including an outer wall extending along an outer peripheral surface of the sponge-like member between the outer and inner sides and located for engagement with the base member.

* * * * *